(12) United States Patent
Claude et al.

(10) Patent No.: US 7,396,582 B2
(45) Date of Patent: Jul. 8, 2008

(54) MEDICAL DEVICE CHEMICALLY MODIFIED BY PLASMA POLYMERIZATION

(75) Inventors: Charles D. Claude, San Jose, CA (US); Jeong S. Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/827,887

(22) Filed: Apr. 6, 2001

(65) Prior Publication Data

US 2002/0146557 A1   Oct. 10, 2002

(51) Int. Cl.
  *B32B 27/32*   (2006.01)
  *B32B 27/00*   (2006.01)
  *A61M 5/32*   (2006.01)
  *A61M 29/00*   (2006.01)

(52) U.S. Cl. ............... 428/220; 428/332; 428/334; 428/500; 604/96.01; 604/103; 604/103.06; 606/194

(58) Field of Classification Search ............... 428/220, 428/332, 334, 335, 336, 339, 411.1, 421, 428/473.5, 343, 500, 515, 474.4, 926; 604/96.01, 604/103, 264, 523, 101.01, 101.02, 103.06, 604/103.07, 103.09, 916; 606/191, 194, 606/192, 193
See application file for complete search history.

(56) References Cited

U.S. PATENT DOCUMENTS

| 4,743,327 | A | | 5/1988 | DeHaan et al. |
| 4,946,903 | A | | 8/1990 | Gardella, Jr. et al. |
| 4,973,394 | A | | 11/1990 | Ross et al. |
| 5,061,738 | A | | 10/1991 | Solomon et al. |
| 5,118,524 | A | | 6/1992 | Thompson et al. |
| 5,376,400 | A | | 12/1994 | Goldberg et al. |
| 5,437,900 | A | | 8/1995 | Kuzowski |
| 5,451,428 | A | | 9/1995 | Rupp |
| 5,455,040 | A | | 10/1995 | Marchant |
| 5,620,649 | A | * | 4/1997 | Trotta .................. 264/515 |
| 5,723,219 | A | | 3/1998 | Kolluri et al. |
| 5,752,934 | A | * | 5/1998 | Campbell et al. ........... 604/96 |
| 5,868,704 | A | | 2/1999 | Campbell et al. |
| 5,876,753 | A | | 3/1999 | Timmons et al. |
| 5,888,591 | A | | 3/1999 | Gleason et al. ........... 427/522 |
| 5,891,114 | A | | 4/1999 | Chien et al. |
| 5,932,299 | A | | 8/1999 | Katoot |
| 5,962,138 | A | | 10/1999 | Kolluri et al. |
| 6,048,620 | A | * | 4/2000 | Zhong .................. 428/424.4 |
| 6,053,939 | A | | 4/2000 | Okuda et al. ............... 623/1 |
| 6,099,563 | A | | 8/2000 | Zhong .................. 623/1.46 |
| 6,139,525 | A | * | 10/2000 | Davis-lemessy et al. .... 604/103 |
| 6,299,596 | B1 | | 10/2001 | Ding |
| 6,306,506 | B1 | | 10/2001 | Timmons et al. |
| 6,447,920 | B1 | * | 9/2002 | Chabrecek et al. ........ 428/423.1 |
| 6,592,550 | B1 | | 7/2003 | Boatman et al. |
| 6,946,173 | B2 | * | 9/2005 | Lim et al. .............. 428/35.2 |

FOREIGN PATENT DOCUMENTS

| WO | WO 91/01210 | 2/1991 |
| WO | WO 97/42257 | 11/1997 |
| WO | WO 99/32235 | 7/1999 |
| WO | WO 0032255 | 6/2000 |

* cited by examiner

*Primary Examiner*—Sheeba Ahmed
(74) *Attorney, Agent, or Firm*—Fulwider Patton LLP

(57) ABSTRACT

Medical devices, and particularly intracorporeal devices for therapeutic or diagnostic uses, having a component chemically modified by plasma polymerization. The medical device comprises a substrate with a plasma polymerized functionality bonded to a surface of at least a section thereof. The plasma polymerized film on a first component of the medical device allows for bonding an agent or a second component to the first component. In one embodiment, the plasma polymerized film facilitates fusion or adhesive bonding of a first component to a second component formed of a material which is dissimilar to, incompatible with, or otherwise not readily bondable to the substrate material of the first component. In another embodiment, a bioactive agent is bonded to the plasma polymerized film on the component, for presenting or delivering the bioactive agent within a body lumen of the patient.

10 Claims, 2 Drawing Sheets

MEDICAL DEVICE CHEMICALLY MODIFIED BY PLASMA POLYMERIZATION

BACKGROUND OF THE INVENTION

This invention generally relates to medical devices, and particularly intracorporeal devices for therapeutic or diagnostic uses, such as balloon catheters.

In percutaneous transluminal coronary angioplasty (PTCA) procedures, a guiding catheter is advanced until the distal tip of the guiding catheter is seated in the ostium of a desired coronary artery. A guidewire, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as DACRON, may be implanted in vessels to strengthen or repair the vessel, or used in an anastomosis procedure to connect vessels segments together.

In the manufacture of catheters, one difficulty has been the bonding of dissimilar materials together. The fusion bonding of a dissimilar material to a substrate material can be extremely difficult if the substrate has a low surface energy. For example, lubricious materials such as HDPE and PTFE, often used to form inner tubular members of catheters to provide good guidewire movement therein, have low surface energies of 31 dynes/cm and 18 dynes/cm, respectively, that make bonding to balloons formed of a dissimilar material such as a polyamide difficult. Prior attempts to address this problem involved providing a multilayered shaft having an outer layer on the shaft configured to be bondable to the balloon. However, a decrease in shaft collapse pressure resistance may result in some cases when the outer layer has a lower stiffness than the a shaft material. While adhesives may be used in some cases to bond dissimilar materials together, they are not ideal because they can increase stiffness of the component at the bond and some materials do not bond well to adhesives commonly used in medical devices.

It would be a significant advance to provide a catheter or other medical device component with improved bondability.

SUMMARY OF THE INVENTION

This invention is directed to medical devices, and particularly intracorporeal devices for therapeutic or diagnostic uses, having a component chemically modified by plasma polymerization. The medical device comprises a substrate with a plasma polymerized functionality bonded to a surface of at least a section thereof. The plasma polymerized functionality generally comprises a film covalently bonded to the substrate. The plasma polymerized film on a first component of the medical device allows for bonding an agent or a second component to the first component. In one embodiment, the plasma polymerized film facilitates fusion or adhesive bonding of a first component to a second component formed of a material which is dissimilar to, incompatible with, or otherwise not readily bondable to the substrate material of the first component. In another embodiment, a bioactive agent, or a spacer attached to a bioactive agent, is bonded to the plasma polymerized film on the component, for presenting or delivering the bioactive agent within a body lumen of the patient.

The plasma polymerized film may comprise a variety of suitable functionalities including carboxylate, amine, and sulfonate groups, which are polymerized on at least a surface of the substrate of the medical device component. In one embodiment, the plasma polymerized film, or functionality thereof, is an acrylate, and preferably acrylic acid. The plasma polymerized film is typically crosslinked to varying degrees depending on the nature of the compounds in the plasma which form the film and the radiofrequency (RF) intensity used in the plasma polymerization process. In a presently preferred embodiment, the degree of crosslinking is minimized in order to maximize the chemical modification, i.e., the amount of the plasma polymerized functionality on the surface of the component. In one embodiment, the degree of crosslinking in the plasma polymerized film is less than about 5%. The medical device component substrate may be formed of a variety of suitable materials including fluoropolymers such as polytetrafluoroethylene (PTFE) or expanded polytetrafluoroethylene (ePTFE), polyolefins such as high density polyethylene (HDPE), and engineering thermoplastic or thermoset polymers such as polyetherether ketone (PEEK) or polyimide.

In one embodiment, the medical device component having a plasma polymerized functionality bonded thereto is a shaft or balloon of an intravascular catheter. However, a variety of medical devices may be chemically modified by plasma polymerization according to the invention, including a cover for a stent, and a vascular graft. Balloon catheters of the invention such as an angioplasty catheter or a stent delivery catheter have a component, such as the catheter balloon, shaft, or a stent cover, which is chemically modified by plasma polymerization, and generally comprise an elongated shaft with at least one lumen and balloon on a distal shaft section with an interior in fluid communication with the shaft lumen. Vascular grafts and stent covers of the invention generally comprise a tubular body formed at least in part of a substrate chemically modified by plasma polymerization. The terminology vascular graft as used herein should be understood to include grafts and endoluminal prostheses which are surgically attached to vessels in procedures such as vascular bypass or anastomosis, or which are implanted within vessels, as for example in aneurysm repair or at the site of a balloon angioplasty or stent deployment. The terminology component as used herein should be understood to include medical devices such as catheters having multiple components, as well as single component devices such as vascular grafts.

In one embodiment, the component is a catheter balloon formed at least in part of ePTFE, which, in accordance with the invention, has a plasma polymerized film on at least one of an inner and an outer surface of the ePTFE. The plasma polymerized film on the ePTFE balloon enhances adhesion of polymeric materials such as elastomers, adhesives, and structural polymers, and agents such as bioactive materials, to the ePTFE balloon. For example, in a presently preferred embodiment, the ePTFE balloon has a plasma polymerized film which facilitates bonding an elastomeric material to the chemically modified surface of at least a section of the ePTFE, so that the porous ePTFE layer can be inflated. Additionally, in one embodiment, the plasma polymerized film facilitates bonding the ePTFE balloon to the catheter shaft. In a presently preferred embodiment, the entire length of the ePTFE layer has the plasma polymerized film. ePTFE is PTFE which as been expanded, and the expanded ePTFE typically has a microporous structure comprising nodes interconnected by fibrils. ePTFE is extremely difficult to bond to, and one difficulty has been adhesively bonding ePTFE, absent some pretreatment causing decomposition of the fibril structure or the use of adhesives interlocking in the pore structure of the ePTFE. Unlike chemical modification involving decomposition (i.e., defluoronation) of the ePTFE using compounds including bases (i.e., alkali metal compounds) such as sodium napthalide, or using irradiation with γ-ray or electron beams, corona discharge, glow discharge or plasma etching processes such as oxygen or trifluoroamine etching, the plasma polymerization chemical modification of the invention has minimal effect on the structural integrity of the ePTFE material. The plasma polymerization of the invention deposits an organic layer onto the ePTFE surface which prevents or inhibits etching of the ePTFE microstructure from occurring during the plasma polymerization process. Thus, in one embodiment, the bulk and the surface of the ePTFE material of the component of the invention has a bulk and a surface in a nondecomposed state. The medical device component of the invention has insubstantial or no etching or decomposition of the node and fibril structure of the component substrate from the plasma polymerization process, so that performance characteristics such as tensile strength or average burst pressure of the component are not disadvantageously effected by the plasma polymerization, unlike the effects caused by defluoronation processes or processes otherwise causing decomposition of the substrate structure. Although discussed primarily in terms of ePTFE, it should be understood that the component of the therapeutic or diagnostic device may comprise other substrates including polyethylene, and other substrates having a node and fibril microstructure such as polypropylene, nylon, and ultrahigh molecular weight polyethylene, where plasma etching or other decomposition processes used to allow adhesive bonding are to be avoided.

In another embodiment, the component is a catheter shaft, which in accordance with the invention has a plasma polymerized film on at least a section thereof. The plasma polymerized film provides for improved ability to bond the catheter shaft section to other device components such as a balloon or a second catheter shaft section. The shaft section having the plasma polymerized film is typically formed of materials such as HDPE, fluoropolymers, polyether ether ketone (PEEK), and polyimide. For example, in one embodiment, the shaft has at least a section formed at least in part of a first polymeric material such as HDPE, bonded to a balloon formed at least in part of a second polymeric material such as a polyamide which is incompatible with the first material, and which thus is not otherwise readily fusion bondable to the first material. The plasma polymerized film provides a surface compatible with the second polymeric material to facilitate fusion bonding thereto. Alternatively, the plasma polymerized film provides a surface which facilitates adhesive bonding the shaft to the second polymeric material. In one embodiment, the surface of a shaft formed of HDPE or fluoropolymer is modified by plasma polymerization according to the invention to provide for bonding to other, typically incompatible materials such as polyamides including nylon and polyether block amide (PEBAX). Similarly, the surface of a shaft formed of PEEK or polyimide, modified by plasma polymerization according to the invention, provides for bonding to other materials such as polyamides including PEBAX. The thin plasma polymerized film provides for improved manufacturability and low profile, and without a disadvantageous decrease in shaft collapse pressure resistance.

The invention also comprises methods of treating a surface of at least a section of a medical device, generally comprising exposing the at least a section to a plasma to form a plasma polymerized film thereon. The thickness of the plasma polymerized film is controlled by the duration of the applied plasma, and in one embodiment the plasma polymerized film is about 10 nm to about 150 nm thick, preferably about 50 nm to about 125 nm thick. The section may be first treated with an argon plasma to prepare the surface prior to exposure to the plasma polymerized film deposition. In one embodiment, the method comprises exposing at least a section of a first component to a plasma to form a plasma polymerized film on the section of the first component, wherein the first component of the therapeutic or diagnostic device is formed at least in part of first polymeric material, and then bonding a second component formed of a polymeric material different from or incompatible with the first polymeric material. In another embodiment, the method comprises exposing at least a section a component to a plasma to form a plasma polymerized film on the section of the component, wherein the component is formed at least in part of a polymeric material having a node and fibril microstructure, without decomposing the polymeric material of the component.

In the plasma polymerization according to the invention, free-radical organic species, such as fragmented acrylic acid, in the plasma will couple with the surface of a substrate such as ePTFE, HDPE, PEEK, or polyimide, resulting in a crosslinked thin film which is covalently bonded to the substrate. Selection of the appropriate RF field strength, monomer, and co-reactant results in a thin surface and polymer bulk film which is rich in the organic functionality, such as carboxylate. The plasma polymerized film exhibits minimum re-organization to minimize its surface energy since the surface has a similar molecular composition as the thin bulk film.

The medical device component of the invention, such as catheter balloons and shafts, stent covers, and vascular grafts, have improved manufacturability and/or performance due to the plasma polymerized film, which allows for bonding of polymeric materials, and agents such as adhesives and bioactive agents to the chemically modified substrate material forming the component. The chemical modification of the invention is a permanent surface modification, unlike plasma etching processes in which any beneficial effects on the surface energy of the substrate quickly decrease as a function of time as described by Yasuda and Sharma, J. Polym. Sci. Polym. Phys., Ed. 19:1285 (1981), incorporated by reference herein. Additionally, the deposition of the plasma polymerized film on the medical device component produces little or no decomposition of the chemical structure of the component substrate material. These and other advantages of the invention will become more apparent from the following detailed description when taken in conjunction with the accompanying exemplary drawings.

DETAILED DESCRIPTION OF THE INVENTION

Figure 1:
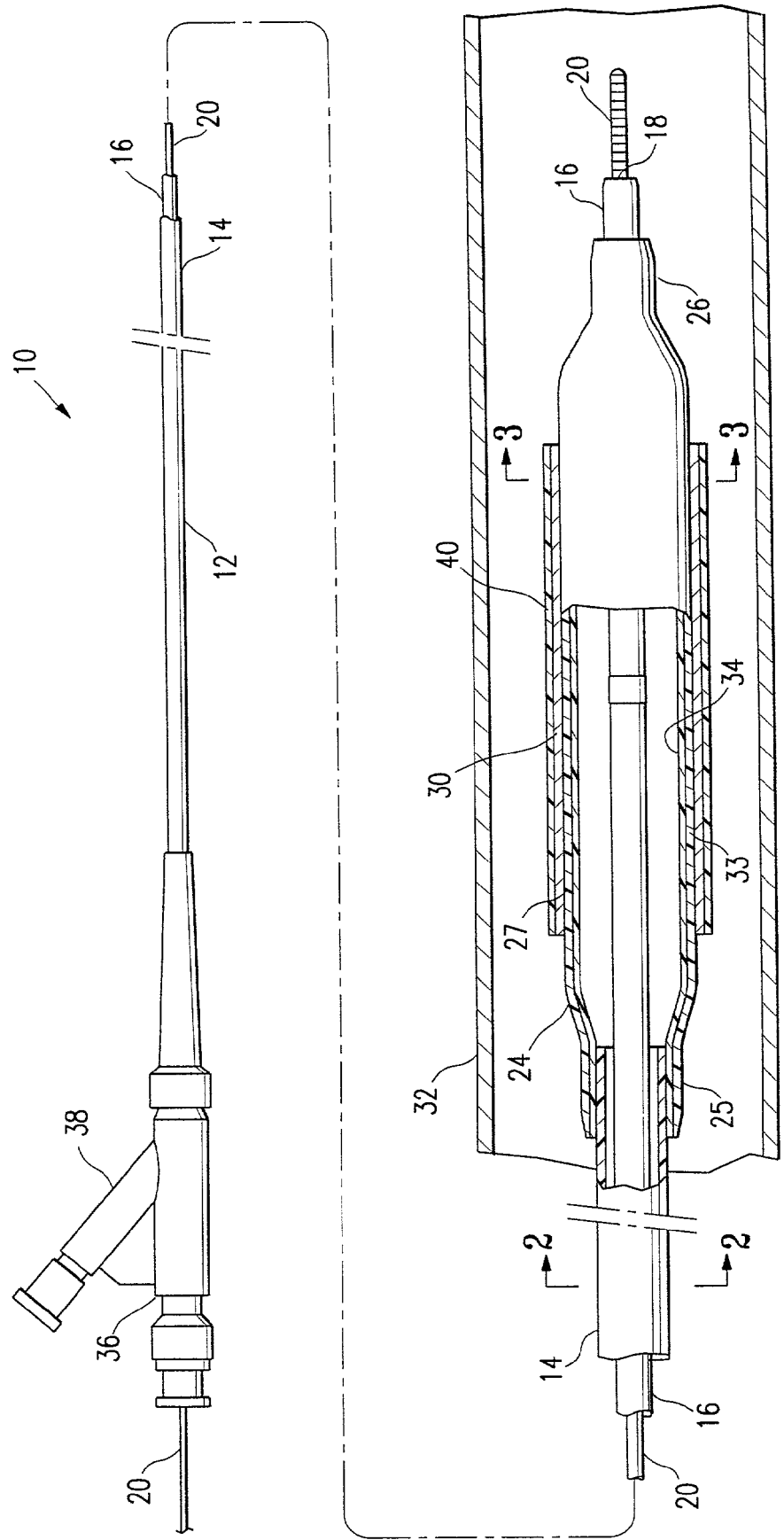
FIG. 1 is an elevational view, partially in section, of a balloon catheter for delivering a stent, that embodies features of the invention.
Figure 3:
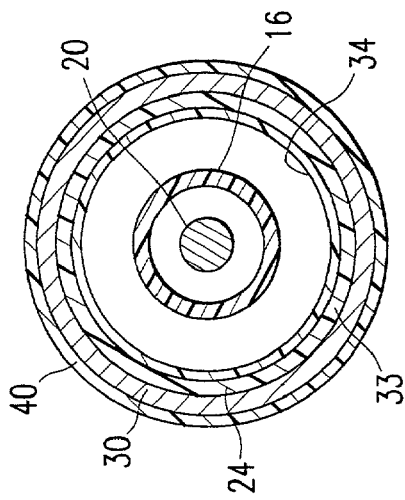
FIG. 3 is a transverse cross-section of the catheter shown in FIG. 1 taken at line 3-3, showing the stent disposed over the inflatable balloon.
Figure 2:
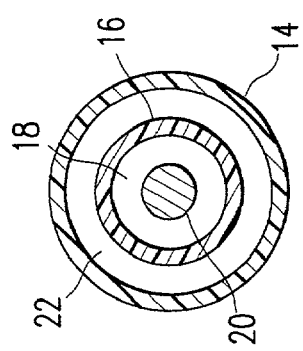
FIG. 2 is a transverse cross-section of the catheter shown in FIG. 1 taken at line 2-2.

FIGS. 1-3 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20. The coaxial relationship between outer tubular member 14 and inner tubular member 16 defines annular inflation lumen 22. An inflatable balloon 24 is disposed on a distal section of catheter shaft 12, having a proximal skirt 25 sealingly secured to the distal end of outer tubular member 14 and a distal skirt 26 sealingly secured to the distal end of inner tubular member 16, so that its interior is in fluid communication with inflation lumen 22. An adapter 36 at the proximal end of catheter shaft 12 is configured to direct inflation fluid through arm 38 into inflation lumen 22 and to provide access to guidewire lumen 18. Balloon 24 has an inflatable working length 27 located between tapered sections of the balloon. An expandable stent 30 is mounted on balloon working length. FIG. 1 illustrates the balloon 24 in an uninflated configuration prior to deployment of the stent 30. The distal end of catheter may be advanced to a desired region of a patient's body lumen 32 in a conventional manner, and balloon 24 inflated to expand stent 30, seating the stent in the body lumen 32.

In the embodiment illustrated in FIG. 1, the balloon 24 comprises a microporous material having a node and fibril microstructure, such as ePTFE. Balloon 24 has a layer 33 of ePTFE, and a second layer 34 formed from a material such as an elastomeric material including polyurethanes such as BIONATE available from PTG or PELLETHANE available from Dow, silicone rubbers, styrene-butadiene-styrene block copolymers, and polyamide block copolymers, and the like. In a preferred embodiment, layer 34 is on the interior of balloon 24, although in other embodiments it may be on the exterior or the balloon 24. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer, or it may at least partially fill the pores of the ePTFE layer. Typically, the ePTFE comprises a film of stretched material which is formed into the tubular member layer 33 by wrapping the ePTFE material around a mandrel to form a tube and then heating the wrapped material to fuse the wrapped material together.

At least a section of the ePTFE of the balloon 24 is chemically modified by plasma polymerization in accordance with the invention. In the embodiment of FIG. 1, the entire length of at least an inner surface of ePTFE layer 33 has a plasma polymerized film, which in accordance with the invention, facilitates bonding layer 33 to layer 34. However, in alternative embodiments, less than the entire length may be chemically modified by masking a part of the substrate using methods conventionally known in the field. Layer 33 is preferably fusion bonded to layer 34. In the embodiment illustrated in FIG. 1, layer 34 is fusion or adhesively bonded to the outer surface of the shaft outer tubular member and inner tubular member to secure the balloon 24 to the shaft. However, in an alternative embodiment, the elastomeric layer 34 does not extend the entire length of the ePTFE layer 33, and the thus exposed one or both end sections of the chemically modified ePTFE layer 33 are fusion or adhesively bonded to the shaft (not shown).

The chemically modified surfaces of the balloon comprise a film (not shown) deposited on the surface of the ePTFE by plasma polymerization. In a presently preferred embodiment, the balloon is chemically modified to create a carboxylate-rich surface. However, a variety of suitable functionalities can be plasma polymerized on the surface of the balloon including amine, and sulfate functionalities. In a presently preferred embodiment, the plasma polymerized carboxylate film comprises an acrylate or acrylate-like polymer layer deposited onto the ePTFE by exposing the ePTFE film to a plasma, which in a presently preferred embodiment is an acrylic acid plasma. One of skill in the art will recognize that some fragmentation of the acrylate typically occurs during plasma polymerization, resulting in an acrylate-like polymer layer of fragmented acrylate. In a presently preferred embodiment, the acrylate is acrylic acid. While discussed below primarily in terms of applying a carboxylate film by plasma polymerization of acrylic acid on ePTFE, it should be understood that a variety of functionalities on a variety of substrates may be used.

In a presently preferred embodiment, the ePTFE is chemically modified to create a carboxylic acid rich surface by exposure to an acrylic acid plasma. In one embodiment, the method comprises introducing the ePTFE into an argon plasma field to remove organic processing debris from the surface of the ePTFE film before deposition of the plasma polymerized film. Preferably, ePTFE film is pre-treated in the argon plasma field at about 200 to 250 mTorr, preferably about 230 mTorr, with an applied RF field of about 100 to 250 W, preferably about 150 W, for about 1 to 3 minutes, preferably about 3 minutes. An acrylic acid plasma is then applied to the ePTFE to produce a carboxylate rich film on the ePTFE. The power of the acrylic acid plasma is about 80 to about 200 W, and preferably about 100 W, with an acrylic acid flow rate of about 0.5 ml/min, at a pressure of about 150 mTorr. The concentration of the carboxylate is dependent on the plasma power, wherein the carboxylate concentration decreases as the RF power increases. The acrylic acid plasma is applied for about 3 to about 10 minutes, preferably about 5 to about 10 minutes, depending on the desired thickness of the carboxylate rich film. The thickness of the carboxylate rich film is about 25 to about 150 nm, preferably about 50 to about 125 nm in the embodiment in which the carboxylate rich film is deposited on a balloon shaft section for bonding to a catheter shaft. In one embodiment, following exposure to the acrylic acid plasma, the plasma field is purged with argon under no RF power to allow surface free-radicals to recombine before exposure to atmospheric oxygen.

In a presently preferred embodiment, carbon dioxide is included in the acrylic acid plasma to limit the rate of decarboxylation from the surface of the ePTFE. The plasma polymerization is a competitive reaction in which polymerization of acrylic acid with surface radical functionalities is greater than the rate of decarboxylation. The decarboxylation of the acrylic acid is caused by fragmentation of the carboxylate, resulting in the formation of carbon dioxide gas and the crosslinking of the deposited film and the loss of carboxylate functionality. Thus, by adding carbon dioxide to the acrylic acid plasma, the decarboxylation of the organic reactive species in the RF field can be decreased. In a preferred embodiment, the carbon dioxide concentration in the acrylic acid plasma is about 8 to about 10%, preferably about 9%.

The plasma polymerization results in a thin carboxylate film deposited onto the substrate. The surface of the substrate has the same polymer composition as the bulk of the substrate, so that the surface and the bulk of the substrate have similar carboxylate concentration following deposition of the plasma polymerized film. The similar carboxylate concentration minimizes the time dependent variation of the surface energy. The structural integrity of the ePTFE layer 33 of the balloon is minimally or not effected by the plasma polymerization.

In the embodiment in which the plasma polymerized film is deposited on an inner surface of the medical device component such as the inner surface of tubular layer 33, the plasma polymerized film is preferably formed using a high pressure RF plasma. For example, in a presently preferred embodiment, a high pressure RF plasma of about 1 atm (760 Torr) to about 1.25 atm (950 Torr), and preferably about 1.05 atm (798 Torr) to about 1.22 atm (927 Torr) is used in embodiments in which the plasma polymerized film is deposited on an inner surface (i.e., a surface defining a medical device lumen) of the medical device component. Specifically, in one embodiment, a plasma polymerized film of acrylic acid is deposited on an inner surface of a tubular substrate according to the following process. Argon and carbon dioxide are bubbled through acrylic acid monomer, at flow rates of about 9.5 to about 15 standard liters per minute (slpm), preferably about 10.5 slpm, and about 0.05 to about 0.2 slpm, preferably about 0.1 slpm, respectively, and through a gas dispersion plate. The argon and carbon dioxide enriched in monomer is then passed through an RF transducer, forming a plasma which is passed through the inner lumen of the substrate. Due to the limited stability of the plasma species, the velocity of the plasma through the inner lumen of the substrate must be sufficiently high that the desired length of the substrate is chemically modified. The velocity of the plasma through the lumen is typically about 30 to about 350 meters per second (m/s), more specifically about 280 to 300 m/s. The pressure of the system is about 1.05 atm (798 Torr) to about 1.22 atm (927 Torr), and the concentration of acrylic acid, which is controlled by the vapor pressure and thus the temperature, is about $5 \times 10^{-5}$ moles/liter of gas.

In another embodiment of the invention, the component chemically modified by plasma polymerization comprises a catheter shaft similar to shaft 12 of FIG. 1. While discussed below in terms of the catheter 10 illustrated in FIG. 1, it should be understood that in the embodiment in which the component chemically modified by plasma polymerization is the catheter shaft, the catheter balloon 24 is not necessarily an ePTFE balloon or a balloon with layer 34 on layer 33. The plasma polymerized film is applied to at least a section of one or both of the outer tubular member 14 and inner tubular member, depending on the purpose of the plasma polymerized film. The film is preferably deposited on an outer surface of the shaft, however, it may be deposited on an inner surface of the shaft, as discussed above in relation to the embodiment having the film deposited on an inner surface of the balloon. To avoid the necessity of masking part of the shaft, the plasma polymerized film may be applied to the entire surface of the shaft, even though it is only needed at the section of the shaft being bonded to another component. The discussion of the plasma polymerized film disclosed above in relation to the embodiment having an ePTFE balloon chemically modified by plasma polymerization applies also to the embodiment having the plasma polymerized film on the shaft. However, because the plasma polymerized film is preferably deposited on an outer surface of the shaft, the plasma is preferably a low pressure RF plasma, and not a high pressure plasma as discussed above. Preferably, a low pressure acrylic acid/carbon dioxide plasma of about 125 mTorr to about 150 mTorr, preferably at least about 145 mTorr (i.e., under vacuum), is used to deposit the carboxylate rich film on the outer surface of the shaft.

In one embodiment, to facilitate bonding the shaft to balloon 24, the plasma polymerized film is applied to at least the distal outer surface of inner tubular member 16. In one embodiment, at least the distal section of the inner tubular member 16 is formed of a lubricious material such as HDPE or a fluoropolymer including PTFE, and has the plasma polymerized film on an outer surface of at least a section thereof. In a presently preferred embodiment, balloon 24 is a single or multilayered balloon, formed of a material dissimilar or incompatible with the substrate material of the inner tubular member 16. For example, balloon material may be a polyamide such as nylon or a polyamide copolymer such as polyether block amide (PEBAX).

The resulting inner tubular member having a chemically modified distal section can be fusion bonded to a polyamide or PEBAX balloon using conventional heat/laser bonding methods. Typically, the balloon distal skirt 26 is placed over the chemically modified distal section of the inner tubular member, and heat applied to the distal skirt 26 to melt or soften the polymeric material. A heat shrink sleeve may also be used during fusion bonding which shrinks to provide pressure at the bond site. The thickness of the plasma polymerized film forming the chemically modified section of the inner tubular member 16 is typically about 50 to about 75 nm. Similarly, a plasma polymerized film can be provided on a surface, and preferably an outer surface, of a distal section of the outer tubular member 14 to facilitate bonding the outer tubular member to the proximal skirt 25 of the balloon 24.

In another embodiment, the plasma polymerized film is deposited on at least a section of the shaft 12 to facilitate bonding a first shaft section to a second shaft section. For example, a proximal shaft section having the plasma polymerized film thereon can be bonded to a distal shaft section formed of a different material than the proximal shaft section. In one embodiment, the proximal shaft section is formed of a polymeric material such as PEEK or polyimide which is stiffer than a material such as PEBAX forming the distal shaft section.

Although discussed primarily in terms of the embodiment in which the first component is fusion bonded to the second component, in an alternative embodiment, the two components are adhesively bonded together after the plasma polymerized film is deposited on the first component. A variety of suitable adhesives commonly used in the medical device field may be used, and the adhesive is applied as is conventionally known by spraying, dipping or otherwise coating a section of the shaft to be bonded.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and wall thickness of 0.004 to 0.008 inch (0.01 to 0.02 cm). The overall length of the catheter 10 may range from about 100 to about 150 cm, and is typically about 135 cm. Preferably, balloon 24 may have a length about 0.5 cm to about 4 cm and typically about 2 cm, and an inflated working diameter of about 1 to about 8 mm, and in a preferred embodiment, an uninflated diameter of not greater than about 1.3 mm. Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials.

In alternative embodiments, the medical device component chemically modified by plasma polymerization in accordance with the invention comprises a stent cover, or a vascular graft. In a presently preferred embodiment, the stent cover or vascular graft comprises a tubular body formed of a substrate comprising ePTFE or other node and fibril material. However, a variety of suitable materials may be used to form the stent cover or vascular graft of the invention. In the embodiment illustrated in FIG. 1, a stent cover 40 is disposed on an outer surface of the stent 30. Stent cover 40 in accordance with the invention has a plasma polymerized functionality bonded to at least a section thereof. Stent cover 40 is secured to the surface of the stent 30 before the stent is introduced into the patient's vasculature, and expanded, together with the stent, to implant the stent and stent cover thereon in the vessel lumen. Stent cover 40 secured to the stent has a generally tubular structure conforming to a surface of the stent. The stent cover 40 length may be selected to fit a variety of conventionally sized stents, with a typical diameter of about 2 mm to about 10 mm. The stent cover 40 wall thickness is typically about 20 μm to about 400 μm, preferably about 40 μm to about 100 μm. The stent cover 40 provides a biocompatible, biostable surface on the stent, and reduces plaque prolapse through the stent struts. A stent cover may be provided on an inner surface of the stent (not shown).

Figure 5:
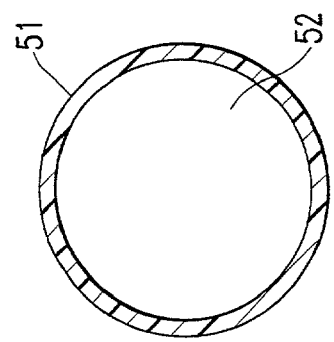
FIG. 5 is a transverse cross-section of the graft or cover shown in FIG. 4, taken along lines 5-5.
Figure 4:
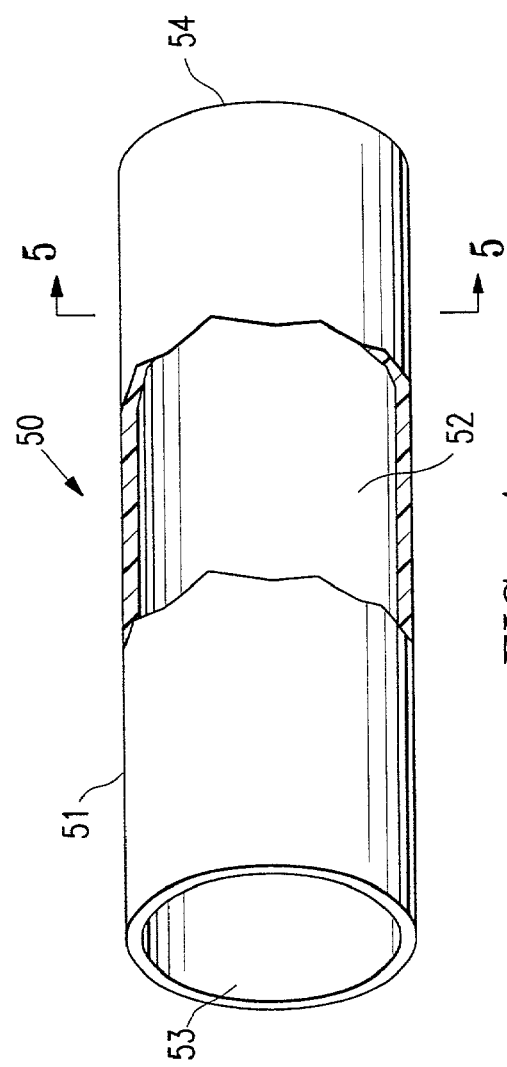
FIG. 4 is an elevational view, partially in section, of a vascular graft or stent cover which embodies features of the invention.

FIG. 5 illustrates vascular graft 50, which in accordance with the invention has a plasma polymerized functionality bonded to at least a section thereof. Vascular graft 50 generally comprises a tubular body 51 having a lumen 52 therein, and ports 53, 54 at either end of the graft 50. The graft is configured for being implanted in the patient, and it may be expanded into place within a vessel or surgically attached to a vessel, such as at a free end of a vessel. The graft 50 length is generally about 4 to about 80 mm, and more specifically about 10 to about 50 mm, depending on the application, and wall thickness is typically about 40 μpm to about 2000 μm, preferably about 100 μm to about 1000 μm. The diameter is generally about 1 to about 35 mm, preferably about 3 to about 12 mm, depending on the application.

A variety of suitable plasma polymerized functionalities may be deposited on the stent cover 40 or vascular graft 50 of the invention, as discussed above in relation to the embodiment having the plasma polymerized functionality on a catheter component. Presently preferred functionalities for the stent cover 40 or vascular graft 50 include an amine functionality such as is derived from allyl amine, and a carboxylate functionality derived from acrylic acid.

In one embodiment, the plasma polymerized film is used to attach bioactive agents, or a spacer or anti-fouling agent such as polyethylene glycol (PEG) attached to the bioactive agent, to the surface of the medical device component. A variety of suitable bioactive agents may be used including antithrombogenic agents, antibiotic agents, antitumor agents, antiviral agents, antiangiogenic agents, angiogenic agents, anti-inflammatory agents such as a superoxide dismutase mimic (SODm), and, most preferably for vascular grafts, cell adhesion promoters such as a RGD (i.e., arginine-glycine-aspartic acid) peptide sequence or RGD mimetic peptide sequence, and the like.

While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter. However, one of skill in the art will readily recognize that other types of intravascular catheters may be used, such as and rapid exchange dilatation catheters having a distal guidewire port and a proximal guidewire port and a short guidewire lumen extending between the proximal and distal guidewire ports in a distal section of the catheter. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising
   a) a multilayer balloon comprising a polymeric first layer having a deposited plasma polymerized polymer film layer of acrylate and fragmented acrylate formed from an acrylic acid plasma and which is covalently bonded to a first surface of the first layer along an entire length of the first layer, and a polymeric second layer, the second layer being bonded to the plasma polymerized film so that the plasma polymerized film is between the first and second layers, and the plasma polymerized film has a thickness which is about 10 to about 150 nanometers; and
   b) an elongated shaft having an inflation lumen, and bonded to the balloon, so that an interior of the balloon is in fluid communication with the inflation lumen.

2. The balloon catheter of claim 1 wherein the first layer is an outer layer of the balloon and the second layer is an inner layer of the balloon, so that the first surface of the first layer which has the plasma polymerized film covalently bonded thereto is an inner surface of the first layer.

3. The balloon catheter of claim 2 wherein the balloon has proximal and distal skirt sections bonded to the shaft, and the inner surface of the first layer along at least a portion of the proximal and distal skirt sections of the balloon has the plasma polymerized film bonded thereto and bonded to the shaft, so that the plasma polymerized film located along the portion of the proximal and distal skirt sections is between the first layer and the shaft.

4. The balloon catheter of claim 1 wherein a fusion bond bonds the first and second layers together.

5. The balloon catheter of claim 1 including a layer of an adhesive between the plasma polymerized film and the second layer, so that the adhesive bonds the second layer to the plasma polymerized film on the first surface of the first layer.

6. The balloon catheter of claim 1 wherein the first layer is formed at least in part of a polymeric material selected from the group consisting of a fluoropolymer, polytetrafluoroethylene, expanded polytetrafluoroethylene, and ultra high molecular weight polyethylene.

7. The balloon catheter of claim 1 wherein the first layer is formed at least in part of a polymeric material having a node and fibril microstructure.

8. The balloon catheter of claim 1 wherein the plasma polymerized film has a thickness of about 50 nm to about 125 nm.

9. The balloon catheter of claim 1 wherein the plasma polymerized polymer film layer further includes crosslinked units, such that the plasma polymerized film is a crosslinked acrylate plasma polymerized film.

10. A balloon catheter, comprising
  a) a multilayer balloon comprising a polymeric first layer having a deposited plasma polymerized polymer film which includes fragmented acrylate formed from an acrylic acid plasma and which is covalently bonded to a first surface of the first layer, and a polymeric second layer, the second layer being bonded to the plasma polymerized film so that the plasma polymerized film is between the first and second layers, and the plasma polymerized film is an acrylate homopolymer and has a thickness which is about 10 to about 150 nanometers; and
  b) an elongated shaft which has an inflation lumen, and which is bonded to the balloon, so that an interior of the balloon is in fluid communication with the inflation lumen.

* * * * *